United States Patent [19]

Mitsumaki et al.

[11] Patent Number: 5,434,083
[45] Date of Patent: Jul. 18, 1995

[54] METHOD AND APPARATUS FOR AUTOMATICALLY ANALYZING A PLURALITY OF TEST ITEMS

[75] Inventors: Hiroshi Mitsumaki, Mito; Katsuaki Takahashi, Katsuta, both of Japan

[73] Assignee: Hitachi, Ltd., Tokyo, Japan

[21] Appl. No.: 19,337

[22] Filed: Feb. 18, 1993

Related U.S. Application Data

[63] Continuation of Ser. No. 551,775, Jul. 12, 1990, abandoned.

[30] Foreign Application Priority Data

Jul. 17, 1989 [JP] Japan .................. 1-182661

[51] Int. Cl.⁶ .......................................... G01N 35/02
[52] U.S. Cl. .............................. 436/48; 436/50; 422/64; 422/67
[58] Field of Search .................. 422/63, 64, 65, 67, 422/116; 436/47–49, 50, 54, 50

[56] References Cited

U.S. PATENT DOCUMENTS

| | | | |
|---|---|---|---|
| 3,617,222 | 11/1971 | Matte | 436/48 |
| 4,340,390 | 7/1982 | Collins et al. | 436/54 |
| 4,699,766 | 10/1987 | Yamashita | 436/48 X |
| 4,781,891 | 11/1988 | Galle et al. | 422/64 |
| 4,837,159 | 6/1989 | Yamada . | |
| 5,104,807 | 4/1992 | Mitsumaki et al. | 422/62 X |
| 5,264,182 | 11/1993 | Sakagami | 422/100 X |

FOREIGN PATENT DOCUMENTS

| | | | |
|---|---|---|---|
| 160458 | 11/1985 | European Pat. Off. . | |
| 0193016 | 9/1986 | European Pat. Off. | 436/48 |
| 316766 | 5/1989 | European Pat. Off. . | |
| 3639399 | 5/1987 | Germany | 436/48 |
| 55-21303 | 2/1975 | Japan . | |
| 57-21663 | 10/1979 | Japan . | |
| 8802866 | 4/1988 | WIPO . | |

*Primary Examiner*—Jeffrey R. Snay
*Attorney, Agent, or Firm*—Fay, Sharpe, Beall, Fagan, Minnich & McKee

[57] ABSTRACT

An annular train of reaction vessels is formed on an intermittently rotatable turntable. In order to measure test items requiring different analysis times, samples and necessary reagents are successively added to the reaction vessels. The analysis times for the test items assigned to the respective reaction vessels are stored in association with positions or numbers of the reaction vessels. Reactions for the test items requiring different analysis times proceed in parallel on the turntable. The reaction vessel whose required analysis time has expired is renewed by a vessel renew device such as a washing device and prepared for receiving the next sample. When a sample for a test item requiring a short analysis time is added to a second reaction vessel after a sample for a test item requiring a long analysis time has been added to a first reaction vessel, the second reaction vessel is renewed earlier than the first reaction vessel.

18 Claims, 7 Drawing Sheets

METHOD AND APPARATUS FOR AUTOMATICALLY ANALYZING A PLURALITY OF TEST ITEMS

This application is a continuation of application Ser. No. 07/551,775, filed Jul. 12, 1990, now abandoned.

BACKGROUND OF THE INVENTION

The present invention relates to a method and apparatus for analyzing a plurality of test items in liquid samples, and more particularly to a method and apparatus suitable for carrying out analysis of a plurality of test items on one reaction vessel train.

As known apparatus for carrying out the analysis for a plurality of test items by an automatic analyzer, a multi-item analyzer which has a plurality of reaction lines in which respective reactions for each test item proceed is disclosed in JP-B-57-21663, and a single-line multi-item analyzer which has only a single reaction line in which reactions for a plurality of test items proceed is disclosed in JP-B-55-21303. The latter is suitable for simplification of construction and it has been widely used.

However, in the prior art single-line multi-item analyzer, the reaction line is composed of a reaction vessel train, and a sample supply device, a reagent supply device and a reaction vessel washing device are fixedly arranged around the reaction line so that each reaction vessel stopped at a reaction vessel washing position is cleaned. As a result, a maximum time period for which the sample may stay on the reaction line is one cycle time of the reaction vessels.

On the other hand, where an extremely small quantity of component in vivo is to be analyzed by utilizing an antigen/antibody reaction, a long reaction time is frequently required. U.S. Pat. No. 4,837,159 discloses an immunological analyzer which separates a bound (B) antigen or antibody, and a free component (F) by cleaning. In the U.S. Patent, reaction containers are arranged on a turntable which forms a circular reaction line and enzyme immuno-assay is carried out on the single reaction line.

In the apparatus of the U.S. Patent, when a first group of samples is to be analyzed, time periods from the sampling to the washing the same for all samples supplied to the reaction line. After the first group of samples has been analyzed, an operating condition of the analyzer is modified for a group of samples to be analyzed next. Because of the modification of the operating condition of the analyzer, the time period from the sampling to the washing is set differently from that under the previous condition. However, the time periods from the sampling to the washing for those samples which are to be processed on the same reaction line are equal to each other.

In the U.S. Pat. No. 4,837,159, the analyzer is first used as a single-line single-item analyzer, and then used as the same analyzer for the next different items. Accordingly, it is very inconvenient when a plurality of test items are to be analyzed for each of many samples.

SUMMARY OF THE INVENTION

It is an object of the present invention to provide a method and apparatus for analyzing a plurality of test items which permit the analysis by applying a proper analysis time to each of samples even if samples for various test items which require different analysis times are placed on one reaction vessel train.

It is another object of the present invention to provide a method and apparatus for efficiently analyzing a plurality of test items when samples for the plurality of test items arranged on one reaction vessel train, which permit changes in stay-times of the vessels in the reaction vessels from test item to test item so that samples requiring a short stay time and samples requiring a long stay time may be mixedly placed.

The present invention is applied to an automatic analyzer which intermittently drives a train of reaction vessels arranged in an endless fashion, causes a sample and a reagent to react in each reaction vessel, and causes any of the reaction vessels on the reaction vessel train to stop at a sample add station and a vessel renew station.

In accordance with the present invention, a plurality of test items which require different analysis times are supplied by sample supply means so that they are mixedly arranged on one reaction vessel train, and the reaction vessels on the reaction vessel train are selectively renewed in a sequence of the time-over of the analysis times of the respective test items.

DESCRIPTION OF THE PREFERRED EMBODIMENTS

A particular test item is related to each of the reaction vessels on a reaction vessel train arranged in an endless fashion to form a reaction line, and when the reaction vessel is exchanged, a new test item is set to the reaction vessel. An analysis time of each of the test items is set to correspond to the number of times of circulation (number of cycles) of the reaction vessels on the reaction line. Each reaction vessel related to the test item has the number of cycles in which it remains on the reaction line controlled by a corresponding pre-inputted analysis condition, and the reaction vessel renew device is selectively controlled for each reaction vessel in accordance with the number of cycles. Thus, in the automatic analyzer, a test item which requires a short reaction time is processed in a smaller number of cycles of the reaction line (usually one cycle), and a test item which requires a long reaction time is processed in a larger number of cycles (usually two cycles or more). Thus, even if a plurality of test items which require different reaction times are requested for one sample, the automatic analyzer can sequentially process them.

In a preferred embodiment of the present invention, an automatic analyzer which handles a plurality of test items on one reaction vessel train comprises a device for inputting an analysis time and the number of reagents to be added for each test item, and a memory for storing the input information. The stored input information and the reaction vessel for the corresponding test item are compared. If the time required for one circulation of the endless reaction vessel train is longer than the analysis time of the test item, the content (reaction liquid) of the reaction vessel is not disposed and the analysis time is extended to the next cycle.

When reactions for the plurality of test items are to proceed on one reaction vessel train, either the sample or the reagent may be applied earlier to the reaction vessel. Means for driving the reaction vessel train is preferably a reaction table which is intermittently rotated by a drive source although any means which cyclically drives the reaction vessel train may be used. For example, separate vessel holders may be coupled in chain and the entire chain rotated, or a plurality of cassette type holders which can accommodate a plurality of reaction vessels may be arranged and they may be rotated to move along a predetermined path. For the sake of explanation, a turntable is used in the following explanation.

The reaction vessel train is intermittently driven along a predetermined path. The path along which the reaction vessel line is driven is usually called a reaction line. Defined on the reaction lines are an agent add station, a sample add station, an agitate station, a measure station and a vessel renew station. At the reagent add station, a reagent for a test item is discharged from a nozzle of an agent add device into the reaction vessel. At the sample add station, a sample picked up from the sample vessel on the sampler is dischaged by a nozzle of a sample add device into the reaction vessel by a predetermined quantity. At the measure station, a light is irradiated to the reaction vessel and a transmitted light or fluorescent light from the reaction vessel is measured. At the vessel renew station, a vessel renew device acts on the stationary reaction vessel. Namely, reaction liquid is ejected from the reaction vessel by a nozzle to dispose the content of the reaction vessel and wash it with a washing liquid, or the reaction vessel which contains the reaction liquid is unloaded for disposition and a new reaction vessel is loaded. An example of the vessel renew device is a reaction vessel washing device or a reaction vessel load/unload device.

Where a reaction table which holds a number of reaction vessels is used, drive and stop functions are applied to the reaction table. In some cases, a vibration may also be applied to the reaction table for the agitation of the reaction table. While the reaction table stops for processing the reaction vessels, processing operations of the respective devices are selectively carried out for the reaction vessels which stop at the reagent add station or the vessel renew station, in accordance with the decision as to whether such processing operations are needed. In this case, the reaction continues in those reaction vessels on the same reaction table for which both the reagents and the samples have already been added.

The analysis time usually means a time period from the renewal of the reaction vessel to the next renewal, but in some cases it means a time period from the first addition of the sample or the reagent into the reaction vessel to the renewal of the vessel. The reaction time usually means a time period from the accommodation of both the sample and the reagent in the reaction vessel to the end of measurement, but in some cases it means a time period from the start of reaction to the renewal of the reaction vessel, or a time period from the start of a specific reaction to the start of a next reaction where a plurality of reactions are included.

In a preferred embodiment of the present invention, after the reaction vessel train has received one or both of the samples and the reagents, the reaction table is driven by one revolution and one vessel pitch and stopped, although the reaction vessel train may be driven in another way, for example, step by step for each vessel pitch or a plural-vessel pitch. One circulation of the reaction vessel train usually means a cycle in which a reaction vessel renewed at the reaction vessel renew station is moved past the sample add station and the reagent add station and stopped at the same vessel renew station. One cycle may also be used to represent the same meaning as one circulation.

In a preferred embodiment of the present invention, even if three or more reagents are to be used for a specific analysis item and the reagents are to be added three times or more, the positions at which the reaction vessels are stopped for the addition of the reagents may be only two on the reaction vessel train. For a test item which requires the addition of the reagents three times, the stored analysis condition and the reaction vessel for the test item are compared, and in the first circulation of the reaction vessel train, the content (including sample, first reagent and second reagent) in the reaction vessel corresponding to the test item is not discarded but is continuously kept in the second and subsequent circulations. In the second and subsequent circulations, a third reagent (and a fourth reagent if necessary) are selectively added to the corresponding reaction vessel.

A memory unit of the automatic analyzer constructed in accordance with the teachings of the present invention comprises a random access memory which allows modification of data and a non-volatile memory such as a floppy disk. The memory unit which comprises these memories stores sample numbers of samples to be processed in the same day, types of test items, a relation between positions of the reaction vessel on the reaction table and the test items, and a control program for the samples. The non-volatile memory stores measurement condition data for each of the test items which may be tested by the analyzer and predetermined operating conditions of the respective elements.

The memory unit stores the information by securing a memory area for the number of times of circulation required for each of the reaction vessels on the reaction vessel train to store measurement data from a detector such as a photometer.

Embodiments of the present invention are now explained with reference to the drawings.

Figure 1:
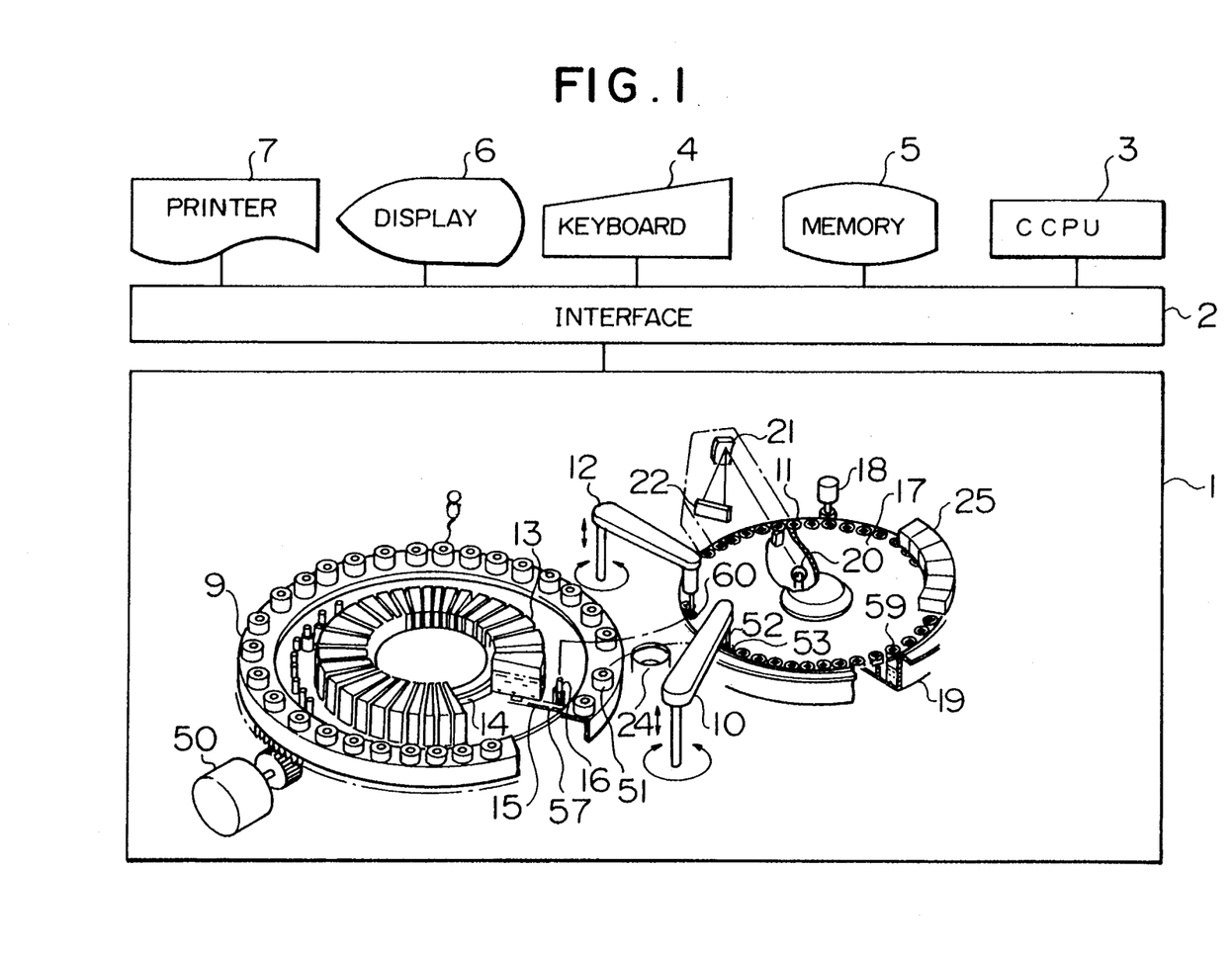
FIG. 1 shows an overall construction of a blood analyzer in accordance with one embodiment of the present invention.

One embodiment of the present invention is now explained with reference to FIGS. 1 to 5. FIG. 1 shows a single-line multi-item automatic chemical analyzer which has only a single reaction vessel train.

In FIG. 1, an analyzer main body 1 accommodates major mechanical elements, the operations of which are controlled by a central processing unit (CPU) 3 through an interface 2. When a sample such as body fluid is to be analyzed, analysis conditions for the respective samples are inputted by a console panel such as a keyboard 4 and are stored in a magnetic storage such as a random access memory 5A or a floppy disk 5B. Results of measurement in accordance with the analysis conditions are displayed on a display unit 6 (for example, a VFD fluorescent display tube) and printed out by a printer 7 for reporting the results.

A sample disk 9 in which a number of sample cups 8 are arranged is driven by a drive unit 50 to position each sample cup to a sample pickup position 51 sequentially. When one of the sample cups 8 which contains the body liquid reaches the sample pickup position and stops, a prescribed amount of sample is sucked into a pipetting nozzle 52 from the sample cup by a sample pipetter 10 which includes a pipetting nozzle 52, and a predetermined amount of sample for the test item is discharged from the nozzle 52 into a reaction vessel 11 which now stops at a discharge position 53 of a sample add station. When the sample in the sample cup which now stops at the pickup position 51 requires a plurality of test items, the sample cup is stopped until the sampling operation by the sample pipetter 10 is carried out as many times as the number of test items. On the other hand, during this period, reaction vessels on a reaction disk 17 are sequentially positioned at a discharge position 53 as many times as the number of items and receive samples for the respective items. After the sampling for the plurality of test items for one sample has been completed, the nozzle of the sample pipetter 10 is positioned at a probe washing unit 24 and it is washed by washing liquid.

The positions of the sample cups on the sample disk 9 are detected by a combination of a rotary detector and a photo-coupler detector as shown in JP-A-56-168555, and they are correlated by the CPU 3.

A reagent disk 14 is arranged on an inner side of the sample disk 9. A number of reagent holders 15 are mounted on the reagent disk 14. A number of reagent bottles having funnel-shaped section which contain reagents necessary for the measurement of the test items are mounted on the holders 15, with openings thereof being held downward. A separate reagent nozzle tip 16 is inserted into an opening 55 (see FIG. 2) of each holder.

Figure 2:
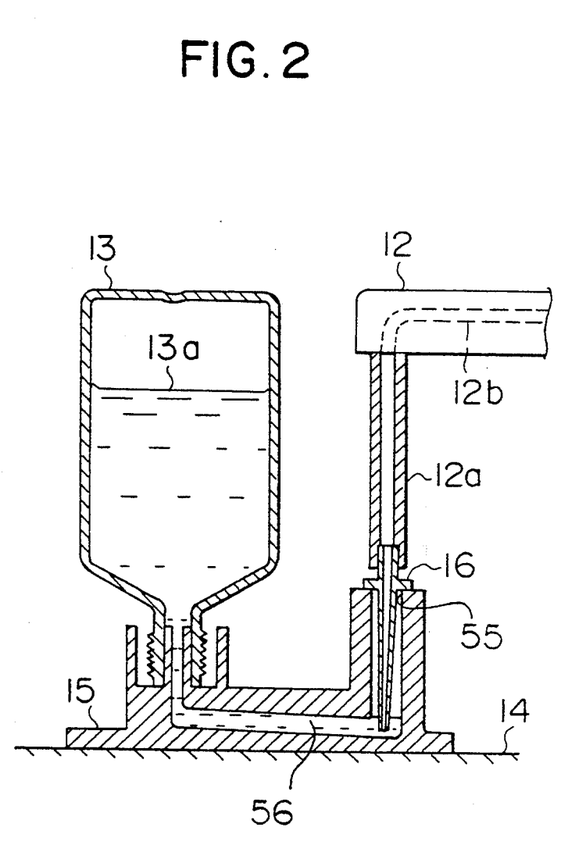
FIG. 2 shows a sectional view of a vicinity of a reagent holder in FIG. 1.

FIG. 2 shows a construction in a vicinity of one of the reagent holders 15. The reagent holders of the same structure are circumferentially arranged on the reagent disk 14. Each reagent holder 15 is hollow and reagent liquid 13a from the reagent bottle 13 is supplied to the opening 55 through a hollow path 56 and it reaches a bottom of the removable nozzle tip 16.

The reagent pipetter 12 in FIGS. 1 and 2 has a nozzle mounting tube 12a which connects to a liquid suck/drain syringe (not shown). When a reagent is to be added to the reaction vessel 11 on the reaction disk 17, the nozzle mounting tube 12a is moved. The reagent disk 14 is driven by a drive unit (not shown) so that the reagent bottle 13 corresponding to the test item for the reaction vessel stops at the reagent suck position 57 as the reaction vessel 11 to which the reagent is to be added is moved and stopped at the reagent add position of the reagent add station. The reagent pipetter 12 supplies a predetermined amount of reagent liquid into the nozzle tip 16 through a plunger hole 12b while the nozzle tip 16 for the corresponding reagent is fitted to the end of the nozzle mounting tube 12a and the nozzle tip 16 is mounted on the opening 55. Then tip 16 is moved to the reaction vessel which is stopped at the reagent add position 60. There, the reagent held in the tip 16 is discharged into the reaction vessel. Then, the tube 12a of the reagent pipetter 12 is moved to the reagent suck position 57 and descended, and the nozzle tip 16 is returned into the opening 55 of the original reagent holder 15.

In FIG. 1, only one reagent supply unit, which comprises the reagent disk 14 and the reagent pipetter 12, is shown, but another reagent supply unit which comprises similar a reagent disk and reagent pipetter is arranged in the present analyzer, although it is omitted for simplication of the drawing. One of the reagent supply unit carries out the addition of a first reagent, and the other reagent supply unit carries out the addition of a second reagent. In this case, the first and second reagent add stations at which the reaction vessels stop are spaced from each other.

Figure 7:
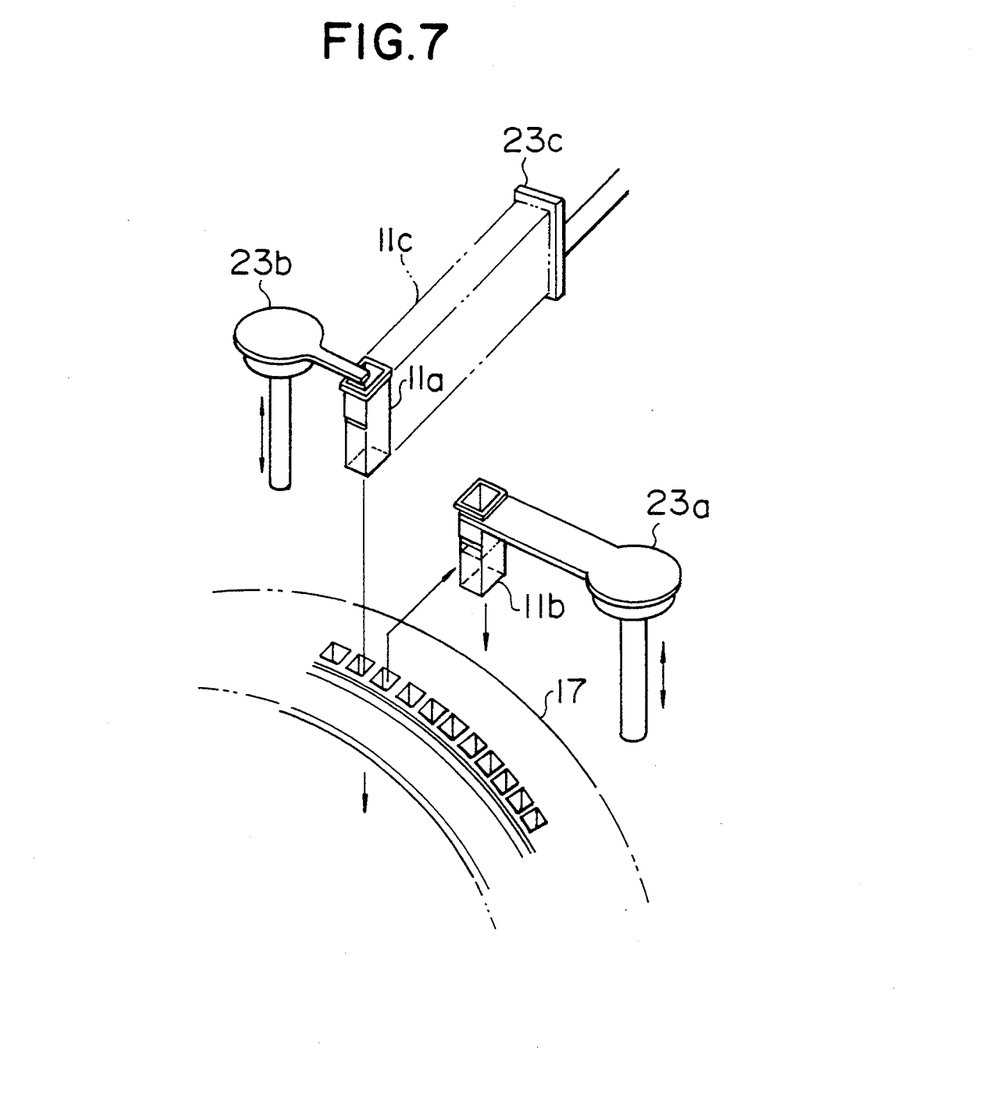
FIG. 7 shows reaction vessel renew means in the analyzer of FIG. 6.

The reaction disk 17 may be rotated clockwise by a stepping motor (not shown). Reaction vessels 11 which are of similar shape as those of the reaction vessels 11a, as shown in FIG. 7, are arranged on the reaction disk 17 at a constant pitch. The reaction vessel train which forms a closed loop is continuously driven by one revolution and one vessel pitch in each interval so that it next stops at an adjacent position to the previous stop position. In effect, it steps. During a stop period between drives, the sample is added, the reagent is added and they are agitated by the agitator 18 at the corresponding station.

The bottom of the reaction vessel train held on the reaction disk 17 is immersed into a constant temperature water tank 19, and the reaction vessel is directly measured at the measure station. A white light beam from a light source 20 of a photometer 58 at the measure station travels across the constant temperature water tank 19 and is directed to a spectroscope where it is spectroscoped by a diffraction grating 21. A plurality of monochromatic lights are detected by a multi-wavelength detector 22 such as a photo-diode array. The measurement is done while the reaction vessel train is driven. Each time one of the reaction vessels 11 moves across the light beam of the photometer, a signal from the detector based on the monochromatic light for measuring the test item of the reaction vessel which has moved across the light beam is selected, converted to a digital signal and stored in a memory 5A or 5B. After a plurality of measurement signals for one reaction vessel have been produced, the CPU 3 calculates a concentration or active value of the corresponding test item, displays a result on the display device 6 and prints it out using the printer 7.

If a particular reaction vessel on the reaction disk 17 is observed, the stop position of the reaction vessel is shifted sequentially and clockwise. In the present analyzer, the stop position of the reaction disk 17 is shifted by one reaction vessel position every 20 seconds. Thus, it takes 960 seconds (16 minutes) to pass through the 48 reaction vessel positions of the circumference. After one circulation of the reaction disk, the reaction vessel is washed by the washing device 25 for reuse.

The washed reaction vessel is prepared for the analysis of the next sample. For the reaction vessel washed by the washing device 25, the first reagent is added at the first reagent add position 59, the sample is added at the sample disharge position 53, and the second reagent is added at the second reagent add position 60. The analyzer is so programmed that when a reaction vessel assigned to a test item which requires a short analysis time is moved around the circumference and stopped at the washing device 25, the washing is carried out, but when a reaction vessel assigned to a test item which requires a long analysis time so that the reaction is not complete at the end of one circulation or to which the reagent is to be added three or more times is moved around the circumference and reaches the washing device 25, the washing device 25 does not carry out the washing.

When a test item which requires a short analysis time is assigned to a second reaction vessel washed by the washing device 25 after the washing of a first reaction vessel, to which a test item which requires a long analysis time has been assigned, the second reaction vessel is renewed by the washing device 25 before the first reaction vessel is next renewed by the washing device 25, and a new test item is assigned to the second reaction vessel. In the analyzer of FIG. 1, once an operator inputs the analysis conditions for the test items for the respective samples, the analyzer controls the respective analysis times to continuously carry out the analysis required for the samples without requesting the operator to classify the samples by their analysis times.

Figure 3:
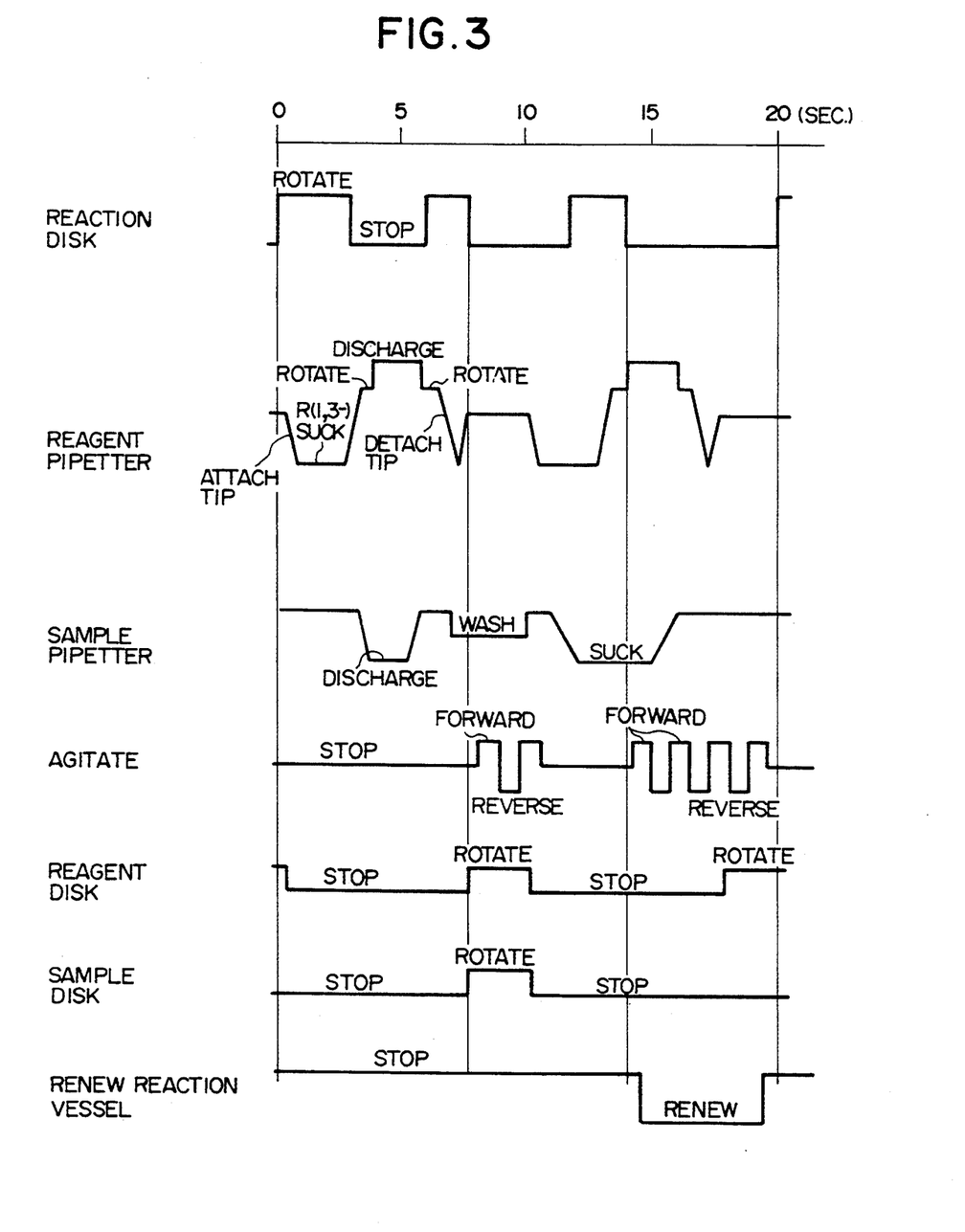
FIG. 3 shows a timing chart for illustrating a relationship among elements of the analyzer in one machine cycle.

FIG. 3 shows a time chart in one machine cycle for illustrating operation timings of the respective elements in the analyzer of FIG. 1.

The detection of all reaction vessels 11 on the reaction disk 17 in the analyzer of FIG. 1 is correlated with the positions of other elements by a microcomputer of the CPU 3 by counting the vessels with reference to one location. A method disclosed in U.S. Pat. No. 4,313,735 may be used to detect the position of the reaction vessel on the reaction disk.

A detection disk for detecting the positions of the reaction vessels on the reaction disk is fixed to a rotary shaft mounted at a rotation center of the reaction disk 17, and a disk-like gear for transmitting a driving force of a stepping motor which serves as a drive source to the reaction disk is also fixed to the rotary shaft. The detection disk has as many detecting holes as the number of reaction vessels on the reaction disk and a light hole for detecting the reference position. Those holes are detected by photo-couplers and detection signals are supplied to the control unit.

In the analyzer of FIG. 1, the control unit 3 detects the numbers or positions of the reaction vessels on the reaction disk 17 based on the detection signals from the photo-couplers and stores them in the memory unit 5. The relationship between the types of test items inputted from the input device 4 and the numbers or positions of the reaction vessels is also stored in the memory unit 5, and the analysis times for the test items are also stored in the memory unit 5. Thus, the control unit 3 may exchangeably assign a test item to each reaction vessel based on the stored information and may correctly control the renewal timing of each reaction vessel.

When a body fluid sample such as blood is to be analyzed by the analyzer of FIG. 1, the operator inputs from the console panel 4 necessary combinations of measurement conditions for all test items to be analyzed by the analyzer. The measurement conditions to be stored in the memory unit 5 may include the renewal time of the reaction vessel, that is, the analysis time, the need for adding the reagents, the codes of reagents to be used, the times to add the sample and the reagent, the measurement mode, the wavelength of the monochromatic light, the amounts of the sample and the reagent to be added and the data processing method.

Once the measurement conditions have been stored for each test item by the input operation, the measurement conditions of the test item are automatically stored in the memory unit 5 by mere selection of the item by the operator through the console panel 4.

When the analyzer is to be operated, the operator inputs the test items required for each sample to be analyzed, through the console panel 4. Based on this input, the microcomputer determines the measurement conditions of each of the test items stored in the memory unit and the measurement sequence in connection with the position of the reaction vessel, and programs how to control the entire reaction line.

When the multi-item analysis operation by the analyzer is started, the sample is sucked and discharged in accordance with the analysis condition, and the first and second reagents are sucked and discharged as required and then they are agitated. If the CPU determines that the addition of a third reagent is necessary or the reaction should be extended beyond 16 minutes, that is, into the second or subsequent circulation, based on the input analysis condition, the reaction vessel does not proceed to the measurement, data processing and washing of the reaction vessel, but the reaction vessel is sent into the next circulation (second circulation) to permit the addition of the third and fourth reagents.

Figure 4:
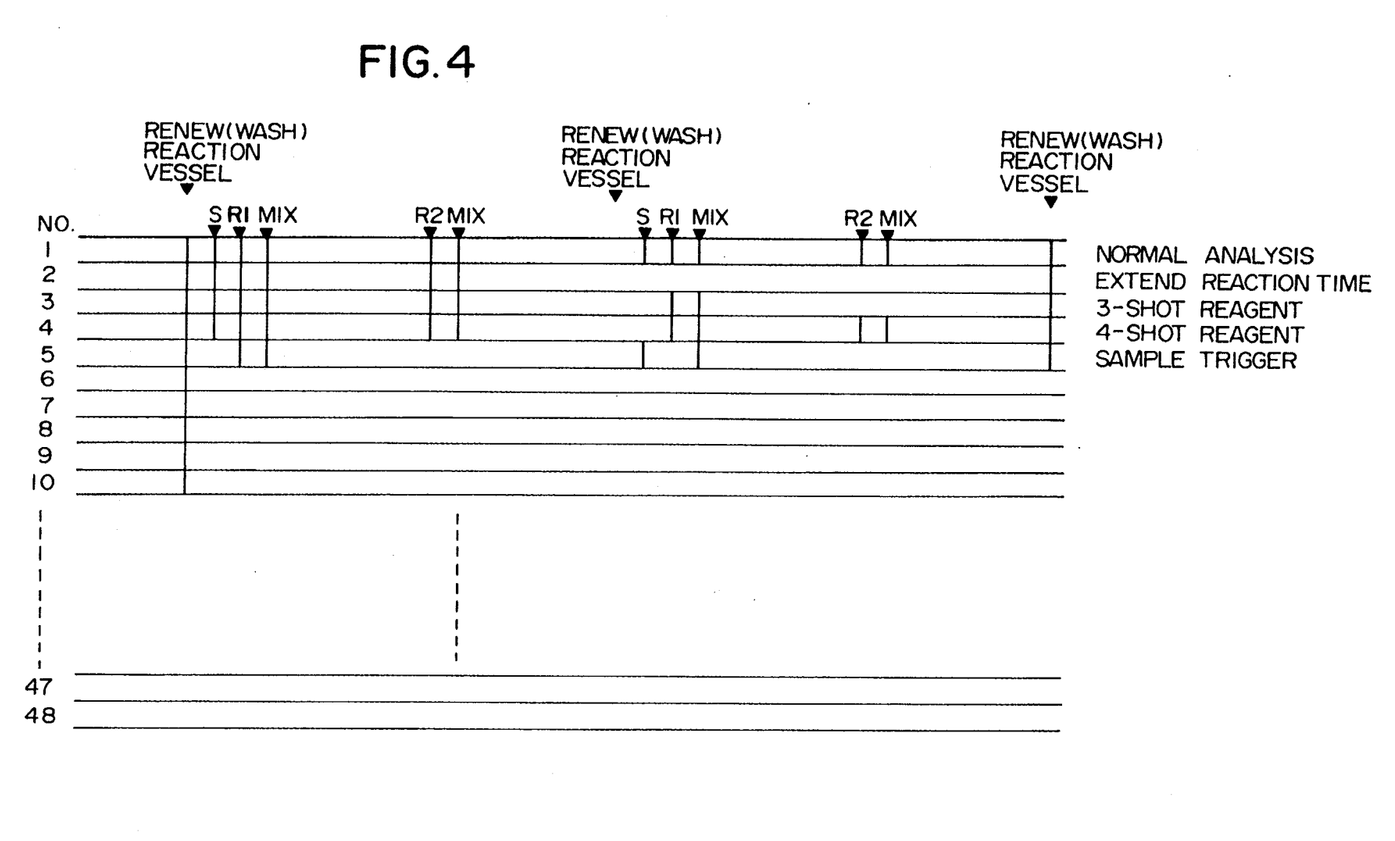
FIG. 4 shows a reaction line control table which is used in multi-item analysis.

FIG. 4 shows an example of a table stored for controlling the reaction line when the multi-item analysis is carried out by the analyzer of FIG. 1. Vertical lines represent operations. In the present example of combination of the analysis conditions, the vessel renew time is delayed 23 seconds, for example, in the cells No. 2 et seq in the actual operation, but they are shown without vessel renew time shift in order to facilitate the comparison of the items. In FIG. 4, the abscissa represents time, S represents the addition of the sample, R1 represents the addition of the first reagent, and R2 represents the addition of the second reagent. MIX represents the mixing. The time period from the first reaction vessel renewal to the next reaction vessel renewal corresponds to one circulation of the reaction vessel train.

In FIG. 4, it is seen that a test item which requires a short analysis time is first assigned to the reaction vessel cell No. 1, and after one circulation, the reaction vessel is washed and renewed, and in a second circulation, a test item which requires a short analysis time for a new reagent is assigned. For a test item assigned to the reaction vessel cell No. 2, the sample and the first and second reagents are added in the first circulation of the reaction vessel train, and the reaction continues in the second circulation. For the test item assigned to the reaction vessel cell No. 3, the sample and the first and second reagents are added in the first circulation, the third reagent is added by the first reagent supply device in the second circulation, and after two circulations, the reaction vessel is renewed. For the reaction vessel cell No. 4, the third reagent is added by the first reagent supply device and the fourth reagent is added by the second reagent supply device in the second circulation.

For the reaction vessel cell No. 5 in FIG. 4, no sample is added in the first circulation of the reaction vessel train but only the first reagent is added, and the sample is added in the second circulation to start the reaction. In this case, the preincuvation of the reagent is facilitated and the measurement of the reagent blank is also facilitated. Up to the cell No. 5, the reaction vessels are circulated up to twice although the circulation of three times or more may be set as required.

Figure 5:
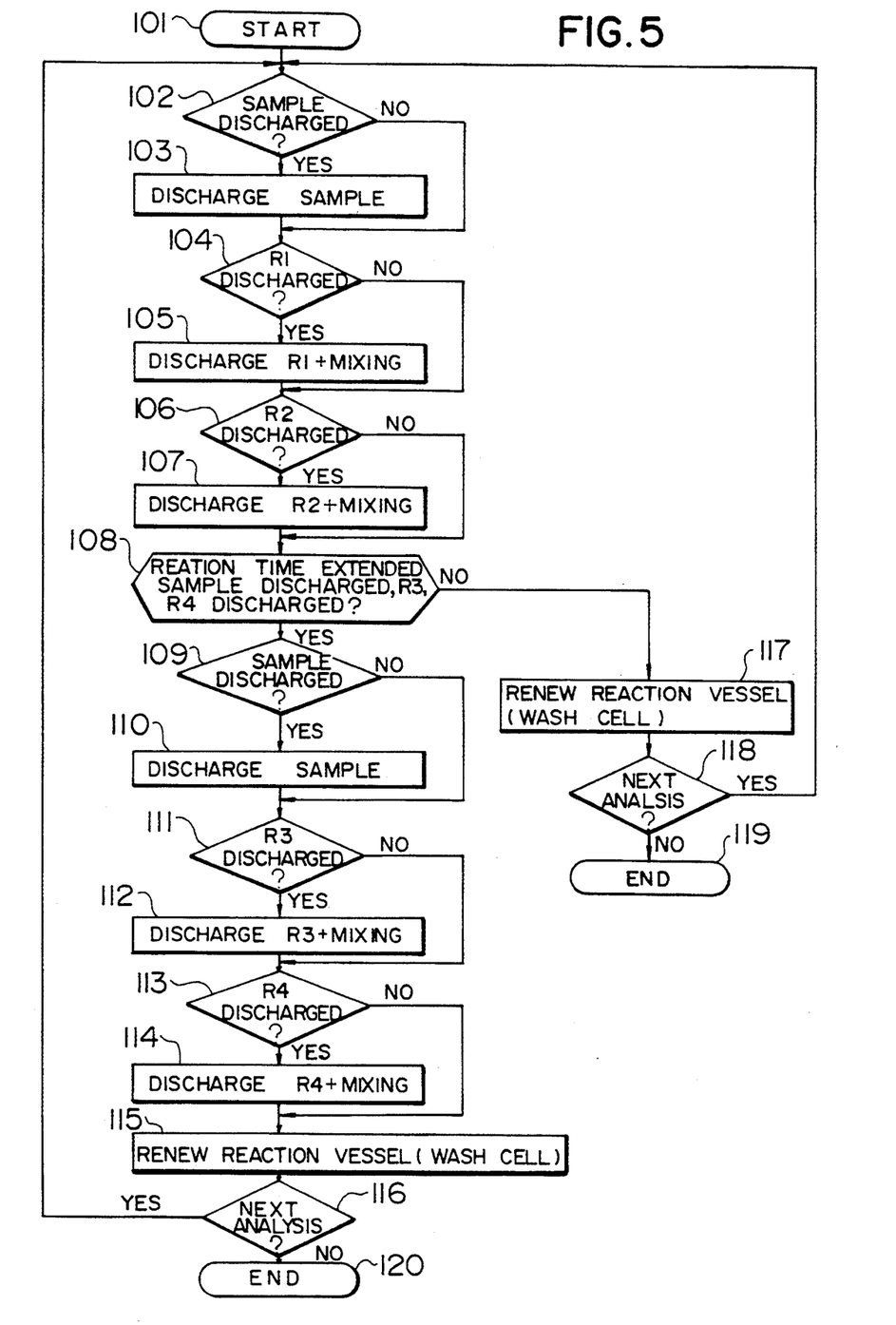
FIG. 5 shows a flow chart of a control method when reactions for a plurality of samples are advanced on a reaction vessel train.

FIG. 5 shows a decision flow chart of a reaction process when the analyzer of FIG. 2 is operated. It shows a process including steps 101 to 120. The decision shown in FIG. 5 is made for each reaction vessel renewed on the reaction disk and the process is carried out by the microcomputer.

By carrying out the process of FIG. 5 for each reaction vessel as the reaction disk 17 is moved, samples are supplied to the reaction vessels such that various items requiring different time periods on the reaction line are mixedly arranged on the reaction disk 17, and proper reaction for each item is carried out under the mixed arrangement. The reaction solutions after the measurement are selectively discharged from the reaction vessels on the reaction table by the washing device 25 in a sequence of expirations of analysis times assigned to the test items and the reaction vessels are washed and renewed. New test items are assigned to the renewed reaction vessel in a sequence of renewal.

Examples of test items requiring a short analysis time are GOT and GPT, and examples of test items which require the analysis time of two or more circulations are cancer embryonic antigen (CEA) and L-malic acid in foods. Of those, the CEA is analyzed by the same control as that for the item analyzed for the cell No. 2 of FIG. 4. The first reagent in the measurement of the CEA is a buffer solution, the second reagent is an antibody sensitive latex solution, and a wavelength for the measurement is 660 nm. In the analysis of the L-malic acid, the fourth reagent is used as it is in the cell No. 4 of FIG. 4. In this case, the first reagent is mixture of buffer solution and L-glutanic acid, the second reagent is an NAD containing solution, the third reagent is a GOT containing solution, and the fourth reagent is an MDH (malic acid dehydrogenated acid) containing solution.

An immunological measurement method which has recently been rapidly developed has been attracting notice as a method which allows detection of an extremely small amount of physiologically active material (holmon, etc.) or a very small amount of disease-related material. A principle of the immunological measurement method is to optically detect a composite selectively coupled to a molecule to be measured by making use of an antigen/antibody reaction which has a very peculiar coupling characteristic. The measurement method which utilizes the antigen/antibody reaction exhibits a high peculiarity but a probability of collision of molecules required for the reaction is proportional to the reaction time because the object to be measured is of low concentration. Thus, in order to attain a sufficient sensitivity, the reaction time should be set long enough to increase the composite of the antigen/antibody.

By applying the present invention, a known oxygen measurement method in which the reaction is completed in approximately 10 minutes and the immunological measurement method which requires an analysis time of 30 minutes or longer may be proceeded in parallel on the same reaction line.

In accordance with the embodiment of FIG. 1, the number of times of circulation may be controlled in accordance with the analysis condition for each reaction vessel in the single-reaction line multi-analysis type automatic analyzer in order to alter the reaction time. Accordingly, the samples which require the analyses under different measurement conditions can be processed in one run. Further, since the reaction time is set by controlling the reaction vessel renew device, there is no waste of time. Since the comparison of the analysis condition is automatically made by the computer, there is no error. From a standpoint of the operator, the operation is same as that of the existing single-line multi-item type automatic analyzer so long as the sample is the same although the analysis condition is different.

Figure 6:
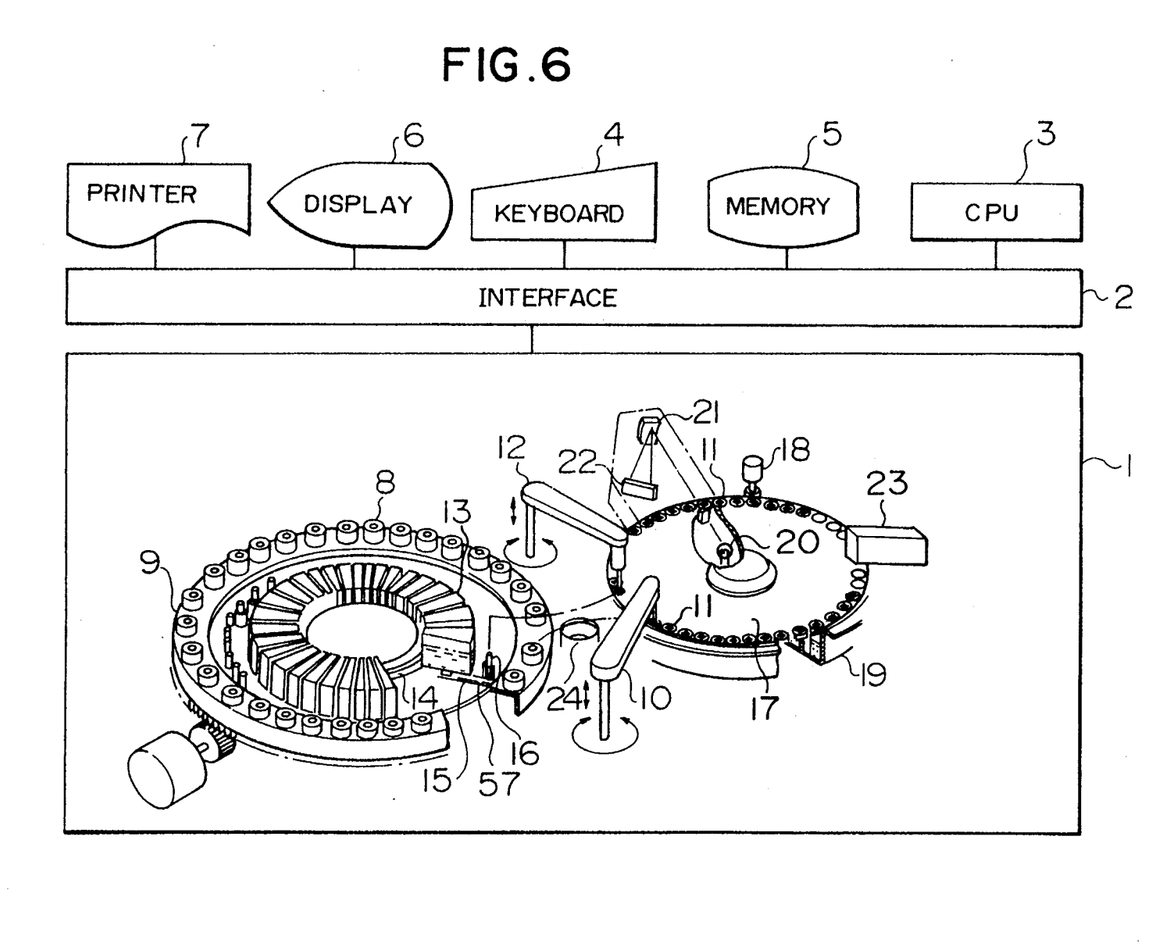
FIG. 6 shows an overall configuration of another embodiment of the present invention.

FIG. 6 shows an overall configuration of another embodiment of the present invention, and FIG. 7 illustrates a vicinity of a reaction vessel loader/unloader of the analyzer of FIG. 6. In the analyzer of FIG. 6, like elements to those of the analyzer of FIG. 1 are designated by like numerals. The analyzer of FIG. 6 differs from that of FIG. 1 in that a loader/unloader 23 for exchanging the reaction vessels in used as a vessel renew device, instead of the washing device.

As shown in FIG. 7, a reaction vessel 11b loaded on the reaction disk 17 is unloaded from the reaction disk by an unloader 23a after the reaction and it is disposed. At the next position, a new reaction vessel 11a is loaded to the empty position by a loader 23b. Unused reaction vessels 11c are in a line and they are fed, one by one, to the loader position by a feeder 23c.

In accordance with the embodiment of FIG. 6, the loader/unloader for the disposable reaction vessels is controlled in accordance with decision information as to whether the reaction is to be extended to the second circulation. Accordingly, the freedom of the analysis method of the automatic analyzer can be improved by a simple mechanical action of disposing or inserting the reaction vessel.

What is claimed is:

1. An automatic analyzer for intermittently transporting a train of reaction vessels arranged in an endless path past a sample add station, a measurement station and a vessel renew station, comprising:

input means for inputting data relating to samples to be tested, and to test items corresponding to each of the samples;

a control unit for receiving data from said input means, and for assigning a sample to be tested, a test item, and an analysis time necessary for analyzing the test item to each of the reaction vessels;

sample cup drive means for sequentially moving sample cups respectively containing different samples to the sample add station;

sample supply means for supplying from a sample cup positioned at the sample add station, the assigned sample to a plurality of reaction vessels corresponding to the test items such that the plurality of reaction vessels respectively assigned with the test items requiring different analysis times for the same sample are mixedly arranged on the reaction vessel train;

a plurality of reagent holders each having an inlet for receiving a respective reagent, an outlet for providing the respective reagent for transfer to a reaction vessel, and a reagent flow path connecting the inlet and outlet;

a plurality of nozzle tips each removably engaging one of the outlets, each outlet tip being dedicated to a single reagent holder;

reagent supply means for supplying each reagent from respective outlets to a respective reaction vessel via the respective nozzle tip, including a nozzle mounting tube, common to all nozzle tips, for engaging a nozzle tip at the respective outlet, drawing means for drawing the reagent into the nozzle mounting tube from the reagent holder via the outlet and nozzle tip, means for moving the engaged nozzle tip from the outlet to the reaction vessel to which the reagent is to be delivered, means for discharging the reagent into the reaction vessel via the nozzle tip, means for returning the nozzle tip to removable engagement with the outlet, and means for releasing the engagement between the reagent delivery means and the nozzle tip so that the nozzle tip is positioned to be employed again for a subsequent reagent delivery; and vessel renew means for selectively renewing the reaction vessels on the reaction vessel train in accordance with the analysis times necessary for analyzing the respective test items, as one of the reaction vessels which conforms to the assigned analysis time is sequentially positioned to the vessel renew station;

wherein said control unit further assigns a new sample, a new test item and an analysis time necessary for analyzing the new test item to the renewed reaction vessel on the reaction vessel train; and wherein said sample cup drive means, when renewed reaction vessels and unrenewed reaction vessels are mixed and included in the reaction vessel train, holds a sample cup containing the new sample at the sample add station until the new sample is delivered to a plurality of renewed reaction vessels corresponding in number to the number of new test items.

2. An automatic analyzer according to claim 1, wherein said vessel renew means includes a reaction vessel wash device for washing selected vessels.

3. An automatic analyzer according to claim 1, wherein the assigned analysis time is a multiple of a minimum vessel renewal time interval required for a reaction vessel to complete a full cycle on the endless path.

4. An automatic analyzer according to claim 1, further comprising:

memory means for storing the analysis times for the respective test items; and control means for controlling the operation of said vessel renew means in accordance with a relationship between a position or number of the reaction vessel to which a sample and a type of test item have been supplied, and the analysis time stored in said memory means.

5. An automatic analyzer according to claim 1, wherein said vessel renew means includes means for renewing the reaction vessel assigned for the test item requiring a shortest analysis time at the first arrival of the reaction vessel to the vessel renew station, and for renewing the reaction vessel assigned for the test item requiring a longer analysis time at a subsequent arrival of the reaction vessel to the vessel renew station.

6. An automatic analyzer according to claim 1, further comprising an intermittently rotatable table on which the reaction vessel train is arranged, and means for optically measuring liquid in each of the reaction vessels during the rotation of the table.

7. An automatic analyzer according to claim 1, wherein the reagent supply means further includes:

a first reagent supply device for supplying reagents firstly and thirdly in time to the reaction vessels on the reaction vessel train; and a second reagent supply device for supplying a reagent secondly in time to the reaction vessels.

8. An automatic analyzer according to claim 1, wherein said vessel renew means includes a reaction vessel exchange device for exchanging a reaction vessel of said reaction vessel train for a reaction vessel that had not previously been part of said reaction vessel train.

9. An automatic analyzer according to claim 1, further comprising a plurality of reagent bottles each having an opening through which a reagent contained therein is delivered to a respective reagent holder, each said reagent bottle being mounted to the respective reagent holder with the opening downward so that the reagent contained in the reagent bottle flows into the reagent holder by force of gravity and forms a pool of constant level from which the drawing means draws the reagent and in which the nozzle tip is operably immersible when removably engaging the outlet.

10. An automatic analyzer according to claim 1, further comprising a plurality of reagent bottles each having an opening through which a reagent solution contained therein is delivered to a respective reagent holder, each said reagent bottle opening being connected to the respective reagent holder with the opening facing downwardly so that the reagent contained in the reagent bottle flows into the respective reagent holder by force of gravity.

11. An automatic analysis method for intermittently transporting a train of reaction vessels arranged in an endless path, causing reaction of a sample and a reagent in each reaction vessel, and stopping one of the reaction vessels on the reaction vessel train at a sample add station and a vessel renew station, comprising the steps of:

inputting data relating to samples to be tested and test items corresponding to each of the samples into a control unit;

assigning, by said control unit, a sample to be tested, a test item, and an analysis time necessary for analyzing the assigned test item to each of the reaction vessels;

sequentially driving a series of sample cups respectively containing different samples to the sample add station;

supplying, from a sample cup positioned at the sample add station, the assigned sample to a plurality of reaction vessels corresponding to the test items such that test items requiring different analysis times are mixedly arranged on the reaction vessel train;

providing a plurality of reagent holders each having an outlet through which a reagent held by the respective reagent holder is supplied for delivery to one of the plurality of reaction vessels;

removably providing a respective nozzle tip for each said outlet;

delivering a reagent supplied at a respective one of the outlets via the corresponding nozzle tip to one of the plurality of reaction vessels by engaging the nozzle tip at the outlet using a nozzle mounting tube common to all nozzle tips, drawing the reagent through the nozzle tip, transporting the reagent and the nozzle tip to the reaction vessel, discharging the reagent into the reaction vessel via the nozzle tip, and returning the nozzle tip to the outlet so that the nozzle tip is positioned to be employed again for a subsequent reagent delivery;

selectively renewing the reaction vessels on the reaction vessel train in a sequence corresponding to expiration of the analysis times for the test items, wherein a new sample, a new test item and an analysis time necessary for analyzing the new test item are assigned by said control unit to a renewed reaction vessel on the reaction vessel train; and for a reaction vessel train having both renewed reaction vessels and unrenewed reaction vessels, holding a sample cup containing the new sample at the sample add station until the new sample is delivered to a plurality of renewed reaction vessels corresponding in number to the number of new test items.

12. An automatic analysis method according to claim 11, further comprising the step of monitoring the analysis times of all reaction vessels on the reaction vessel train.

13. An automatic analysis method according to claim 11, wherein when a second reaction vessel renewed after a first reaction vessel is assigned for a test item requiring a short analysis time, the second reaction vessel is renewed earlier than the next renewal of the first reaction vessel.

14. An automatic analysis method according to claim 11, wherein a cycle from the start of a reaction vessel from the vessel renew station to the next stop at the vessel renew station is continuously repeated over a plurality of cycles, a reagent is added to the reaction vessel in a subsequent cycle, and liquid in the reaction vessel is optically measured in each cycle.

15. An automatic analysis method according to claim 11, further comprising the step of storing, in a memory unit, a position or number of each reaction vessel on the reaction vessel train and an associated analysis time for the test item assigned to each reaction vessel.

16. An automatic analysis method according to claim 11, further comprising the step of determining the necessity of addition of a sample to a reaction vessel as the reaction vessel on the reaction vessel train is positioned to the sample add station, and adding the sample only when the necessity is determined.

17. An automatic analysis method according to claim 11, further comprising the step of providing a reagent bottle for each said reagent holder so that a reagent contained in each reagent bottle flows into the respective reagent holder by force of gravity to form a pool of reagent having a constant level from which the reagent is drawn via the corresponding nozzle tip and in which the corresponding nozzle tip is operably immersed when removably provided to the outlet.

18. An automatic analysis method according to claim 11, further comprising the step of connecting a reagent bottle to each said reagent holder so that a reagent solution contained in each said reagent bottle flows through a downwardly facing opening into the respective reagent holder by force of gravity.

* * * * *